United States Patent [19]

Again et al.

[11] Patent Number: 5,158,764
[45] Date of Patent: Oct. 27, 1992

[54] DENTIFRICE

[75] Inventors: Ivan Again; Vera Boyanova, both of Sofia, Bulgaria; Karin Otto, Hanau, Fed. Rep. of Germany; Matthias Neumüller, Hasselroth, Fed. Rep. of Germany; Harald Dippmann, Hanau, Fed. Rep. of Germany

[73] Assignee: Degussa, Fed. Rep. of Germany

[21] Appl. No.: 771,971

[22] Filed: Oct. 9, 1991

[30] Foreign Application Priority Data

Oct. 9, 1990 [DE] Fed. Rep. of Germany ........ 4031953
Apr. 22, 1991 [DE] Fed. Rep. of Germany ........ 4113044

[51] Int. Cl.$^5$ ............................ A61K 7/16; A61K 7/26
[52] U.S. Cl. ............................................ 424/58; 424/49
[58] Field of Search ..................................... 424/49-58

[56] References Cited

U.S. PATENT DOCUMENTS

| | | | |
|---|---|---|---|
| 1,275,779 | 8/1918 | Spies et al. | 424/49 |
| 1,565,864 | 7/1925 | Putt | 424/49 |
| 1,591,727 | 7/1926 | Nitardy | 424/49 |
| 1,716,035 | 6/1929 | Donchi | 424/49 |
| 2,343,651 | 3/1944 | Fielding | 424/49 |
| 3,431,339 | 3/1969 | Gyarmathy et al. | 424/49 |
| 3,440,065 | 4/1969 | La Via | 514/781 |
| 4,159,345 | 6/1979 | Takeo et al. | 514/781 |
| 4,181,712 | 1/1980 | Rialdi | 424/49 |
| 4,269,859 | 5/1981 | Morse | 514/781 |
| 5,039,526 | 8/1991 | Grodberg et al. | 424/435 |

FOREIGN PATENT DOCUMENTS 2625676 7/1989 France .

OTHER PUBLICATIONS

European Search Report.
Chemical Abstracts published by the American Chemical Society vol. 99 (Dec. 12–Dec. 26) (Abstracts 195423–224469) 1983 pp. 1 and 370.
Chemical Abstracts published by the American Chemical Society vol. 112 (Jun. 18–Jun. 25) (Abstracts 229187–245501) 1990 pp. 1 and 110.
Article entitled "Materials Chemistry and Physics" vol. 13 No. 1 Jul. 1985 an international journal pp. 502–517.

Primary Examiner—Shep K. Rose
Attorney, Agent, or Firm—Cushman, Darby & Cushman

[57] ABSTRACT

A dentifrice consists of the customary known non-abrasive dentifrice components which contains cellulose powder instead of customary known polishing bodies as the abrasive component.

6 Claims, No Drawings

DENTIFRICE

The present invention relates to a dentifrice for removing plaque which is employed as an actively prophylactic, hygienically cosmetic and healing preparation in daily use and in stomatologic practice.

BACKGROUND OF THE INVENTION

It is known that cellulose powder with a particle size of 1 to 350 micrometers can be used for direct tableting of medications. This eliminates additional auxiliary measures and the use of additional adjuvants based on the specific rheologic parameters of powdery cellulose.

The selection of suitable agents which effectively eliminate plaque is essential in the production of hygienic and prophylactic agents of the buccal cavity such as the dentifrices used daily, with varying active prophylactic and cosmetic effect.

To this end, it is known that scouring agents such as calcium carbonate, dicalcium phosphate dihydrate, among others, are used which, even though they eliminate the plaque on the teeth due to their mechanical action, damage at the same time the hard enamel to a varying degree.

The use of microcrystalline cellulose such as e.g. AVICEL PH 105 as abrasive component in toothpastes is known. See published French application 2,625,676.

SUMMARY OF THE INVENTION

The object of the present invention is to provide an effective, plaque-cleaning agent for the buccal cavity which does not cause any undesired side effects on the hard enamel and which preserves the normal physiological state of the buccal cavity.

These and other objects are achieved with a dentifrice consisting of the customary known components of a dentifrice but which contains cellulose powder instead of known abrasive components as the cleaning agent.

The cellulose powder can have a particle size of 1 to 300 micrometers, preferably of 35 to 160 micrometers and can be contained in the dentifrice in an amount of 1 to 25% by weight, preferably of 10 to 20% by weight.

In one embodiment of the invention, microfine powdery cellulose can be used as the sole cleaning body. Other additional active substances which are plaque-removing, plaque-preventing or infection-inhibiting can be eliminated.

A cellulose powder which is sold under the name ELCEMA® P 050 and P 100 and has the following physical properties is preferred:

Native, high-percentage α cellulose consisting of 1,3-β-glycosidically linked D-glucose molecules with n=primarily around 500 and above.

Fine white powder
  without taste or odor
  insoluble in water
  insoluble in dilute acids
  swelling in dilute alkalies
  insoluble in organic solvents

| ELCEMA ® type | P 100 | P 050 |
|---|---|---|
| Structure | powder | powder |
| Particle size in microns approx. | 50–150 | 40–70 |
| Bulk weight when bagged g/l | approx. 220 | approx. 230 |
| pH | 5.0–7.5 | 5.0–7.5 |
| Refractive index | 1.55 | 1.55 |
| Density g/cm$^3$ | approx. 1.5 | approx. 1.5 |

| | |
|---|---|
| Drying loss 2 h/105° C. | <6% |
| Residue on ignition 2 h/850° C. | <0.3% |
| Water-soluble components | <1.0% |
| Ether-soluble components | <0.15% |
| Calcium ions | <0.05% |
| Chloride ions | <0.05% |
| Sulfate ions | <0.05% |
| Heavy-metal ions as Pb | <10 ppm |
| Zn | <2 ppm |
| As | <1 ppm |
| Cr | <1 ppm |
| Fe | <10 ppm |
| Cu | <1 ppm |

Demonstration of identity

The substance dissolves slowly in ammoniacal copper oxide solution. No violet or blue coloration occurs with iodine solution in aqueous dispersion.

The cellulose powder which can be used in accordance with the invention is described in the "Deutsches Arzneibuch", 9th edition, 1986 (DAB9) on page 621, in the USP XXII NF XVII (The United States Pharmacopeia, The National Formulary), 1990, page 1916 and in the European Pharmacopoeia, 2nd edition, part. II, eighth edition 1984, page 315.

It has been determined in tests performed with dentifrices in accordance with the invention, with cellulose powder which exhibited a particle size of 1 to 350 micrometers, that they effectively eliminate plaque, prevent it from reforming and act in an infection-inhibiting manner in the buccal cavity when used in amounts of 1 to 25% by weight, preferably 10 to 20% by weight in various compositions of dentifrices. In addition, there is compatibility with all biologically active components such as: Fluoride ions, zinc ions chemical therapeutic agents, enzymes, components of natural origin which can be used in addition, if necessary, for a greater inhibition of the development of plaque and which also can exhibit an infection-inhibiting action.

The cellulose powder is chemically inert and at the same time physiologically compatible. These properties make it possible to use it in oral hygiene formulations whose contents are incompatible with known cleaning agents. It is known, for example, that fluorine compounds retain their action only for a limited time in combination with known cleaning agents such as calcium carbonate, di-calcium phosphate-di-hydrate and others. In the combination of the cellulose powder with dentifrices containing fluoride ions, dentifrices are formulated which retain the activity of the fluoride for an unlimited time span, at least, however, for 18 months. This makes it possible to produce dentifrices without having to take into consideration the previously necessary limitations on their ability to be stored.

In a preferred embodiment of the invention the cellulose powder can be used in fluorine-containing dentifrices.

DETAILED DESCRIPTION OF PREFERRED EMBODIMENTS

The invention is illustrated in the following examples:

| Example 1 | % by weight |
|---|---|
| ELCEMA ® P 100 | 10.0 |
| Glycerol | 20.0 |
| Aerosil ® 200 | 1.0 |
| Blanose | 1.5 |
| Sweetener | 1.0 |
| Preservative | 0.5 |
| Aroma substance | 1.0 |
| Foaming agent | 1.0 |
| Water up to | 100 |

| Example 2 | % by weight |
|---|---|
| ELCEMA ® P 100 | 20.0 |
| Glycerol | 10.0 |
| Aerosil ® 200 | 1.0 |
| Blanose | 1.5 |
| Sweetener | 1.0 |
| Preservative | 0.5 |
| Aroma substance | 1.0 |
| Foaming agent | 1.5 |
| Water up to | 100 |

| Example 3 | % by weight |
|---|---|
| ELCEMA ® P 050 | 15.0 |
| Glycerol | 20.0 |
| Aerosil ® 200 | 3.0 |
| Blanose | 1.5 |
| Preservative | 0.5 |
| Aroma substance | 1.0 |
| Sweetener | 1.0 |
| Foaming agent | 1.5 |
| Water up to | 100 |

The substances used in the examples can be characterized as follows:

Aerosil ® 200 is a pyrogenically produced silica with a BET surface of $200 \pm 25$ m$^2$/g.

Blanose is a sodium carboxymethylcellulose used as a binder.

The sweetener is saccharine.

The preservative is Nipagin and Nipasol, which constitutes 0.1% by weight together, or sodium benzoicum (0.5% by weight).

The aroma substance is peppermint oil.

The foaming agent is sodium lauryl sulfate. ELCEMA ® P 100 or P 050 is a native, high-percentage α-cellulose consisting of 1,4-β-glycosidically linked D-glucose molecules with n=primarily around 500 and above. Fine white powder
without taste or odor
insoluble in water
insoluble in dilute acids
swelling in dilute alkalies
insoluble in organic solvents

| ELCEMA ® type | P 100 | P 050 |
|---|---|---|
| Structure | powder | powder |
| Particle size in microns approx. | 50-150 | 40-70 Bulk |
| weight when bagged g/l | approx. 220 | approx. 230 |
| pH | 5.0-7.5 | 5.0-7.5 |
| Refractive index | 1.55 | 1.55 |
| Density g/cm$^3$ | approx. 1.5 | approx. 1.5 |

| Drying loss 2 h/105° C. | <6% |
|---|---|
| Residue on ignition 2 h/850° C. | <0.3% |
| Water-soluble components | <1.0% |
| Ether-soluble components | <0.15% |
| Calcium ions | <0.05% |
| Chloride ions | <0.05% |
| Sulfate ions | <0.05% |
| Heavy-metal ions as Pb | <10 ppm |
| Zn | <2 ppm |
| As | <1 ppm |
| Cr | <1 ppm |
| Fe | <10 ppm |
| Cu | <1 ppm |

Demonstration of identity

The substance dissolves slowly in ammoniacal copper oxide solution. No violet or blue coloration occurs with iodine solution in aqueous dispersion.

In order to test the chemical purity of ELCEMA ®, the following test methods of the following pharmacopoeias can be used:
"Deutsches Arzneibuch", 9th edition, 1986 (DAB9), page 621,
USP XXII NF XVII (The United States Pharmacopeia, The National Formulary), 1990, page 1916
European Pharmacopoeia, 2nd edition, part. II, eighth edition, 1984, page 315.

The following activities are investigated in the clinical testing of the dentifrice:
Plaque removal, plaque prevention and inhibition of inflammation.

The testing is carried out on 40 persons, 25 to 35 years of age. The persons tested are healthy in body, without deformation of face and jaw, without caries, without fillings in their teeth and with slightly defined catarrhal gingivitis. A preliminary hygienic preparation is carried out by removing plaque and tartar. The test begins three days after this preliminary treatment and 12 hours after the last brushing of the teeth. The following values are determined:
OHI-S according to Green and Vermillion
PMA according to Massler and Schour
The number of migrated leucocytes, the flaked-off epithelial cells, the erythrocytes in the mouth liquid according to Jasinovski.

The monitoring of brushing takes place according to the instructions in accordance with "Methoden fur die klinische Studie von Zahnpasten", Moscow-Sofia, 1980.

The test is started with the registration of the PL plaque index and the GI inflammation index.

The plaque removal and the plaque prevention are measured according to the following method:

The test groups and control groups clean their teeth regularly in the course of 4 weeks with toothpaste using new toothbrushes. The teeth are cleaned twice a day for three minutes per time under supervision. The evening brushing is carried out on all tooth surfaces with intensive horizontal, vertical and circular motions.

10 to 12 brushes are used in each of the two sections:

$$\frac{876}{876} \quad \frac{54}{54} \quad \frac{321}{321} \quad \frac{123}{123} \quad \frac{45}{45} \quad \frac{678}{678}$$

The registration of the plaque index is carried out at the start of the test (diagnostic index) on a tooth which is not brushed for one night, and at the end of each week. The plaque is dyed by sucking on a standard dyeing tablet until completely dissolved. The plaque index is determined according to the method of Green Vermillion (simple index).

The plaque coating of the vestibular surfaces of $$\frac{6\ 16}{1}$$

becomes, just as the coating of the intermediary spaces as well as the coating of the surfaces located on the tongue side with a value of $$\overline{6\ 6}:$$

—0—no plaque detected
—1—plaque on 1/3 of the tooth surface
—2—plaque on 2/3 of the tooth surface
—3—plaque on the entire tooth surface The plaque is determined after 1 to 4 weeks in percent relative to the original state.

The degree of inflammation is carried out on 20 test persons who participate in the plaque test and exhibit a slightly defined, chronic gingivitis.

The PMA index is determined at the start and after 1 to 4 weeks. The gums are treated with $J_2$-KJ solution according to the method of Svrakov-Pissarev and the inflammation determined around $$\frac{616}{616}$$

in accordance with the following values:
—0—no inflammation observed
—1—gingival papilla inflamed The PMA index is compared after 1 to 4 weeks in percent to the initial state. The values determined for the dentifrice of the invention are compared with the values of known dentifrices determined in parallel. The following results are obtained:

| Dentifrice with cleaning bodies | Plaque removal | Plaque prevention | Inflammation-inhibiting effect in the buccal cavity |
|---|---|---|---|
| 1. Calcium carbonate | 32.38% | 11.03% | 5–10% |
| 2. Dicalcium phosphate dehydrate (Benckiser-Hoechst) | 42.13% | 10.18% | 5–10% |
| 3. Precipitated silica (Sident ® 9, Degussa) | 38.52% | 10.15% | 5–10% |
| 4. Microcrystalline cellulose (Micricel) | 32.15% | 5.12% | 5–10% |
| 5. Cellulose powder (Elcema ®, Degussa) | 78.16% | 20.04% | 28–33% |

The table shows that dentifrice 5 with ELCEMA ® (cellulose powder according to the invention) has a surprisingly high plaque-removing action in comparison to dentifrices 1, 2, 3 and 4. Dentifrice 5 also clearly exceeds dentifrice 4, which contains microcrystalline cellulose (Microcel) according to the state of the art.

The unexpectedly high values for the plaque-preventing effect and the inflammation-inhibiting effect are especially surprising. In addition, a healing action occurs in the buccal cavity.

The microcrystalline cellulose Micricel used in dentifrice 4 is the same product as AVICEL. AVICEL is a microcrystalline cellulose which was partially purified and depolymerized before the spray drying (cf. The National Formulary XIII edition, monograph 43).

The stability test of dentifrices containing fluoride ions which contain cellulose powder as abrasive component carried out with the aid of accelerated aging methods and using the Arhenius equation shows that in dentifrices with sodium fluoride and with sodium monofluorophosphate, the active fluorine and monofluorophosphate ions retain their quantity unchanged for a time span of more than 3 to 4 years.

What is claimed is:

1. In a dentifrice consisting essentially of a polishing agent and conventional non-abrasive dentifrice components;
   the improvement in which the polishing agent is a cellulose powder having the following characteristics:
   Structure: powder
   Particle size in microns, approximately 40–150
   Bulk weight when bagged g/l, approximately 220–230 pH 5.0–7.5
   Refractive index 1.55
   Density g/cm$^3$ approximately 1.5
   Drying loss after 2 hours at 105° C. <6%
   Residue on ignition 2 hours/850° C. <0.3%
   Water-soluble components <1.0%
   Ether-soluble components <0.15%
   Calcium ions <0.05%
   Chloride ions <0.05%
   Sulfate ions <0.05%
   Heavy metal ions as Pb<10 ppm
   Zn<2 ppm
   As<1 ppm
   Cr<1 ppm
   Fe<10 ppm
   Cu<1 ppm 2. A dentifrice as set forth in claim 1 in which said polishing agent is present in an amount of 1 to 25% by weight.

3. A dentifrice according to claim 1 in which the cellulose powder is present in an amount of 10 to 20% by weight.

4. A method of removing or preventing plaque on the teeth which comprises applying to the teeth a dentifrice according to claim 1.

5. A method of inhibiting inflammations in the buccal cavity which comprises applying a dentifrice according to claim 1 to the buccal cavity.

6. A method of removing or preventing plaque on the teeth which comprises brushing the teeth with a dentifrice as set forth in claim 1.

* * * * *